(12) United States Patent
Reid

(10) Patent No.: US 8,568,365 B2
(45) Date of Patent: Oct. 29, 2013

(54) METHODS AND APPARATUS FOR SYRINGE ADAPTER

(76) Inventor: Alan Reid, Keene, NH (US)

( * ) Notice: Subject to any disclaimer, the term of this patent is extended or adjusted under 35 U.S.C. 154(b) by 89 days.

(21) Appl. No.: 11/745,672

(22) Filed: May 8, 2007

(65) Prior Publication Data

US 2008/0281264 A1 Nov. 13, 2008

(51) Int. Cl.
*A61M 5/32* (2006.01)

(52) U.S. Cl.
USPC ......... 604/198; 604/110; 604/187; 604/192; 604/197; 604/218; 604/256; 604/263; 604/275; 604/200; 604/245; 604/190

(58) Field of Classification Search
USPC ......... 604/110, 187, 192, 197, 256, 263, 275, 604/198, 200–245, 190
See application file for complete search history.

(56) References Cited

U.S. PATENT DOCUMENTS

| | | | | |
|---|---|---|---|---|
| 3,144,866 A | * | 8/1964 | Ellis | 604/212 |
| 3,306,291 A | * | 2/1967 | Burke | 604/110 |
| 3,938,898 A | * | 2/1976 | Reitknecht | 401/183 |
| 4,084,588 A | * | 4/1978 | Koenig | 604/205 |
| 4,365,626 A | * | 12/1982 | House | 604/190 |
| 4,735,618 A | | 4/1988 | Hagen | |
| 4,792,053 A | * | 12/1988 | Towns et al. | 215/250 |
| 4,874,383 A | * | 10/1989 | McNaughton | 604/198 |
| 4,888,001 A | | 12/1989 | Schoenberg | |
| 4,927,417 A | * | 5/1990 | Moncada et al. | 604/198 |
| 4,944,731 A | | 7/1990 | Cole | |
| 5,060,704 A | * | 10/1991 | Rohrbough | 141/312 |
| 5,135,507 A | | 8/1992 | Haber et al. | |
| 5,147,319 A | | 9/1992 | Ishikawa et al. | |
| 5,192,275 A | | 3/1993 | Burns | |
| 5,217,437 A | * | 6/1993 | Talonn et al. | 604/198 |
| 5,279,576 A | * | 1/1994 | Loo et al. | 604/187 |
| 5,338,306 A | | 8/1994 | Srivatsa | |
| 5,415,645 A | * | 5/1995 | Friend et al. | 604/110 |
| 5,445,619 A | | 8/1995 | Burns | |
| 5,531,709 A | * | 7/1996 | Eykmann et al. | 604/218 |
| 5,536,253 A | | 7/1996 | Haber et al. | |
| 5,607,398 A | | 3/1997 | Parmigiani | |
| 5,713,872 A | | 2/1998 | Feuerborn et al. | |
| 5,743,888 A | * | 4/1998 | Wilkes et al. | 604/198 |
| 5,879,330 A | | 3/1999 | Bell | |
| 5,925,029 A | * | 7/1999 | Jansen et al. | 604/411 |
| 5,951,522 A | | 9/1999 | Rosato et al. | |
| 5,957,895 A | | 9/1999 | Sage et al. | |
| 5,992,899 A | * | 11/1999 | Strowe | 285/93 |
| 5,997,504 A | | 12/1999 | Bell | |
| 6,017,329 A | * | 1/2000 | Hake | 604/198 |
| 6,156,012 A | | 12/2000 | Nathan | |

(Continued)

OTHER PUBLICATIONS

Dictionary.com. "Disengage } Define Disengage at Dictionary.com." Accessed online Dec. 17, 2011. <http://dictionary.reference.com/browse/disengage>.*

(Continued)

*Primary Examiner* — Nicholas Lucchesi
*Assistant Examiner* — Scott Medway
(74) *Attorney, Agent, or Firm* — Daly, Crowley, Mofford & Durkee, LLP

(57) ABSTRACT

Methods and apparatus for a syringe adapter. In one embodiment, an adapter/cap assembly is threadably engaged to a syringe for enteral feeding applications. The adapter cannot be removed from the syringe to prevent the syringe from being used for IV applications.

3 Claims, 5 Drawing Sheets

(56) References Cited

U.S. PATENT DOCUMENTS

| | | |
|---|---|---|
| 6,210,371 B1 | 4/2001 | Shaw |
| 6,258,078 B1 * | 7/2001 | Thilly ............................ 604/411 |
| 6,287,282 B1 * | 9/2001 | Bonaldo et al. ............... 604/198 |
| 6,319,233 B1 * | 11/2001 | Jansen et al. .................. 604/192 |
| 6,344,031 B1 * | 2/2002 | Novacek et al. .............. 604/195 |
| 6,454,745 B1 * | 9/2002 | Donnan et al. ................ 604/181 |
| 6,500,155 B2 | 12/2002 | Sasso |
| 6,568,439 B1 * | 5/2003 | Se et al. ......................... 141/301 |
| 6,663,604 B1 | 12/2003 | Huet |
| 6,755,805 B1 | 6/2004 | Reid |
| 6,969,375 B2 * | 11/2005 | Thibault et al. ............... 604/241 |
| 7,001,364 B1 * | 2/2006 | Farhi .............................. 604/198 |
| 7,314,464 B2 * | 1/2008 | Giambattista et al. ........ 604/198 |
| 2001/0021827 A1 | 9/2001 | Ferguson et al. |
| 2004/0122375 A1 * | 6/2004 | Woodard et al. .............. 604/218 |
| 2004/0199085 A1 * | 10/2004 | Young et al. ................... 600/576 |
| 2006/0106349 A1 * | 5/2006 | Kito et al. ...................... 604/187 |
| 2006/0135910 A1 | 6/2006 | Luther et al. |

OTHER PUBLICATIONS

Millennium Medical, Huber Plus Safety Infusion Set, Jan. 2000, 1 Page, Chadds Ford, Pennysylvania.

* cited by examiner

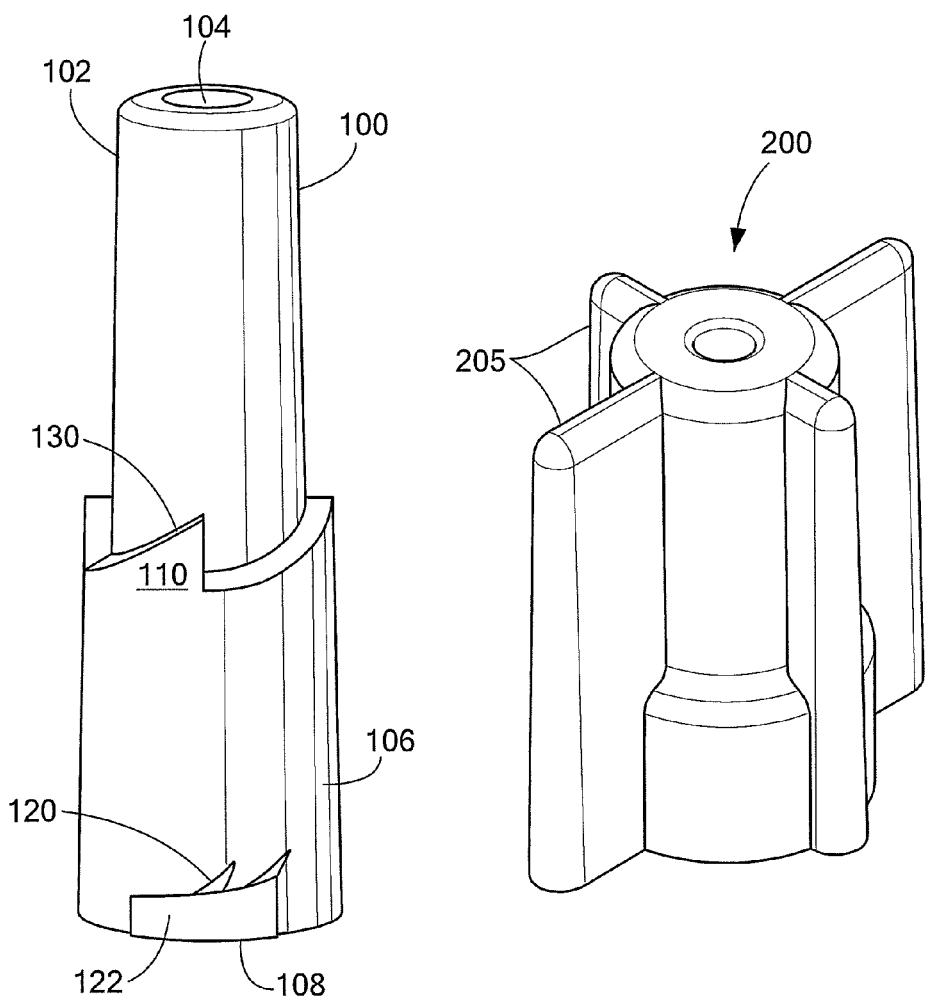

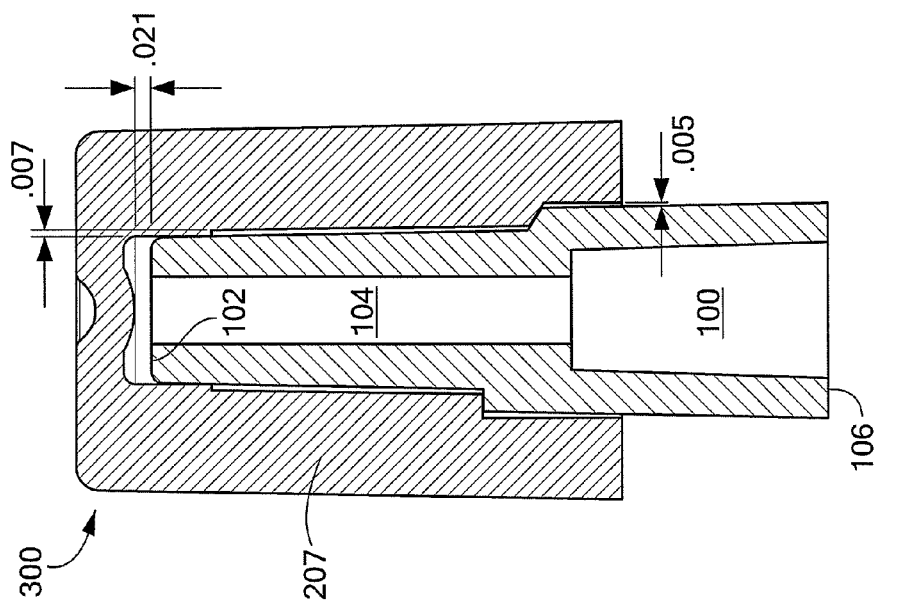
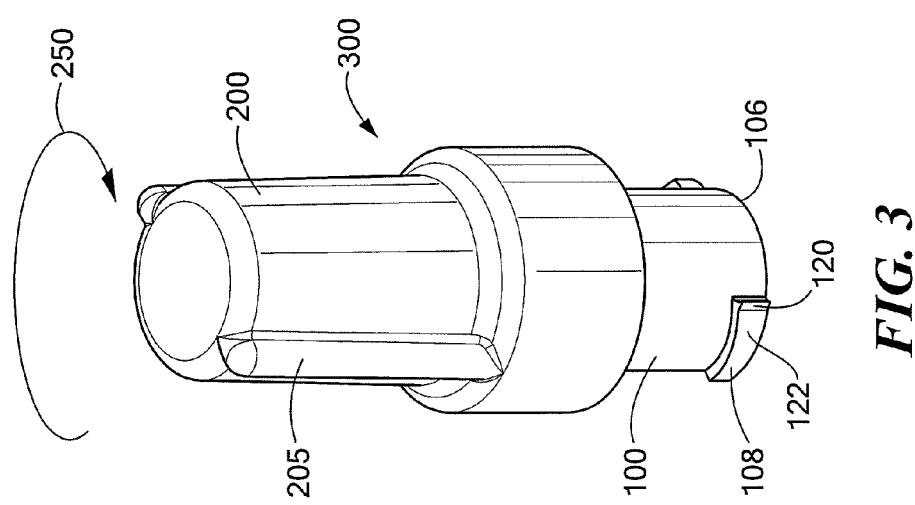
FIG. 3
FIG. 3A

METHODS AND APPARATUS FOR SYRINGE ADAPTER

BACKGROUND

As is known in the art, a variety of syringes are used for medical applications. For example, an enteral syringe can be filled with nutritional material that can be ingested by a patient via a feeding tube. Another type of syringe having a threaded end to engage with a complementary end is used to provide solution intravenously. It is further known that an IV (intravenous) syringe can be filled with a substance, such as breast milk for an infant, and then misused as an IV syringe. This can lead to disastrous results including death due to substances being injected directly into a patient's vein.

SUMMARY

The present invention provides methods and apparatus to adapt a syringe for enteral applications where the adapted syringe cannot be used for IV applications after being adapted. In exemplary embodiments, an assembly includes an adapter and a cap, where the cap is used to rotate the adapter onto threads of the syringe for permanent engagement to the syringe to enable enteral feeding applications of the syringe. Rotation of the cap in the opposite direction removes the cap from the adapter to allow fluid egress from the syringe.

In one aspect of the invention, an assembly comprises an adapter having a first end and a second end and a cap engagement mechanism, the first end having a mating mechanism to engage a syringe, and a cap having an adapter engagement mechanism to engage the cap engagement mechanism of the adapter, wherein the adapter mating mechanism is configured to engage the syringe by rotation of the adapter in a first direction and to resist rotation of the adapter in a second direction opposite the first direction.

The assembly can further include one or more of the following features: the cap engagement mechanism and the adapter engagement mechanism are configured to rotate the adapter in the first direction by rotation of the cap in the first direction, rotation of the cap in the second direction disengages the cap from the adapter, the cap and adapter form a seal that is broken by rotation of the cap in the second direction, the first end includes a tip configured for enteral feeding, the cap engagement mechanism includes at least one tooth, the adapter engagement mechanism includes at least one tooth to engage the at least one tooth of the cap engagement mechanism, the mating mechanism includes one or more barbs to provide unidirectional rotation of the adapter when engaging the syringe, and the one or more barb extends from at least a partial thread.

In another aspect of the invention, a device comprises an adapter having a first end and a second end, the first end having a mating mechanism to engage a syringe, and wherein the adapter mating mechanism is configured to engage the syringe by rotation of the adapter in a first direction and to resist rotation of the adapter in a second direction opposite the first direction.

In a further aspect of the invention, a method comprises providing an adapter having a first end and a second end and a cap engagement mechanism, the first end having a mating mechanism to engage a syringe, and providing a cap having an adapter engagement mechanism to engage the cap engagement mechanism of the adapter, wherein the adapter mating mechanism is configured to engage the syringe by rotation of the adapter in a first direction and to resist rotation of the adapter in a second direction opposite the first direction.

BRIEF DESCRIPTION OF THE DRAWINGS

The foregoing features of this invention, as well as the invention itself, may be more fully understood from the following description of the drawings in which:

FIG. 1 is a perspective schematic depiction of a syringe adapter in accordance with exemplary embodiments of the invention;

FIG. 2 is a perspective schematic depiction of a syringe adapter cap in accordance with exemplary embodiments of the invention;

FIG. 3 is a perspective schematic depiction of a syringe adapter/cap assembly in accordance with exemplary embodiments of the invention;

FIG. 3A is a cross-sectional view of a syringe cap/adapter assembly in accordance with exemplary embodiments of the invention;

DETAILED DESCRIPTION

FIG. 1 shows an exemplary embodiment of a syringe adapter 100 and FIG. 2 shows an exemplary embodiment of a cap 200 that is matable with the syringe adapter 100. The adapter/cap assembly 300 of FIG. 3 can be coupled to a syringe 10, shown in FIG. 4, to safely adapt the syringe for enteral feeding applications, as described in detail below.

Figure 4:
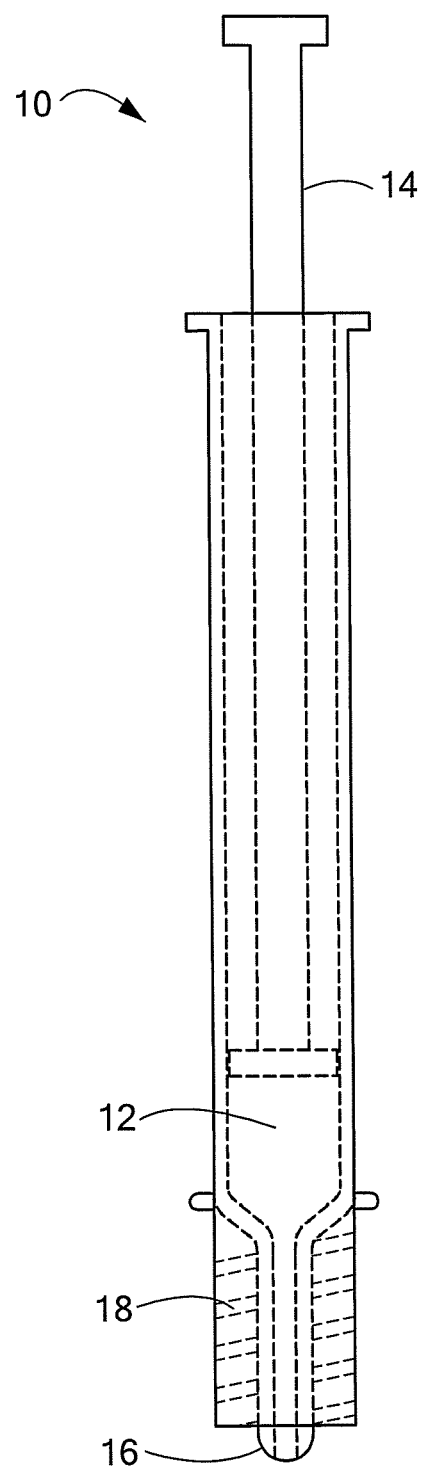
FIG. 4 is a schematic depiction of a prior art syringe to which a syringe adapter can be attached in accordance with exemplary embodiments of the invention.

The adapter/cap assembly 300 can be secured to the syringe 10 of FIG. 4. The syringe 10 can be a conventional IV syringe having a fluid reservoir 12 from which liquid is forced out by depressing a plunger 14. Fluid exits the syringe 10 via a tip 16 in communication with the fluid reservoir 12. A distal end of the syringe includes internal threads 18 to receive a device having complementary threads.

As described in detail below, the adapter/cap assembly 300 can be threadably engaged with threads 18 on the syringe to enable the syringe to be safely used for enteral feeding since the adapter 100 (FIG. 1) cannot be non-destructively removed from the syringe 10. Since the adapter 100 cannot be removed, after enteral feeding applications, the syringe cannot be used for IV applications. In an exemplary embodiment, the adapter 100 and/or the cap 200 can be colored orange, at least in part, to indicated enteral feeding equipment.

Referring to FIGS. 1-4, including FIGS. 3A-3D, the adapter 100 includes a first end 102 having an opening 104 and a second end 106 with a mating mechanism 108 to engage threads 18 of the syringe 10 in a unidirectional attachment. More particularly, the mating mechanism 108 is configured to engage the threads 18 as the adapter 100 is turned in a first direction until full engagement is achieved. Once attached, however, the mating mechanism 108 of the adapter prevents the adapter 100 from being turned in the opposite direction. That is, the adapter 100 cannot be unthreaded from the syringe 10.

In an exemplary embodiment the mating mechanism 108 includes one or more barbs 120 extending from an end of a partial thread 122 extending from the body of the adapter 100. The barb 120 and thread 122 engage the threads 18 on the syringe. The barb(s) 120 resist movement in the opposite direction so that the adapter 100 remains secured to the syringe 10.

It is understood that the mating mechanism can be provided in a variety of alternative suitable configurations that provide the desired one-way, permanent engagement of the adapter 100 to the syringe 10.

In an exemplary embodiment, the adapter 100 is engaged with the syringe 10 by means of a cap 200 coupled to the adapter. The adapter 100 includes a cap engagement mechanism 110 to engage the cap. The cap 200 includes a complementary adapter engagement mechanism 202 (FIG. 3C, 3D) to engage the cap engagement mechanism 110 so that rotation of the cap in a first direction 250 causes the adapter mating mechanism 108 to engage the threaded end 12 of the syringe. Rotation of the cap 200 in the opposite direction causes the cap to be dislodged from the adapter 100. With this arrangement, the cap 100 provides a uni-directional ratchet. Wings 205 on the cap 200, can facilitate rotation of the cap and assembly.

In one embodiment, the cap engagement mechanism 110 includes teeth 130 formed about the adapter 100. The teeth 130 transition a diameter for the tapered first end 102 to a diameter for the tapered second end 106, where the first end is smaller in diameter than the second end.

In an exemplary embodiment, the cap 200 includes an interior surface 210 having the adapter engagement mechanism 202 in the form of teeth 212 to engage the teeth 130 of the cap engagement mechanism of the adapter. While the cap 200 is coupled to the adapter 100, rotation of the cap 200 in a first direction 250 causes the adapter 100 to rotate and thereby be threaded onto the syringe. However, rotation of the cap 200 in the opposite direction causes the cap to disengage from the adapter 100 as the teeth of the 130 of the adapter cap engagement mechanism push off the teeth 212 of the cap adapter engagement mechanism 202.

It is understood that the cap and adapter engagement mechanisms can be provided in configurations other than complementary teeth. Other suitable one-way ratchet mechanisms will be readily apparent to one of ordinary skill in the art without departing from the present invention.

In one embodiment, the cap engagement mechanism 110 and the adapter engagement mechanism 202 provide a seal. In one embodiment, the seal is provided by an interference fit between the cap 200 and the adapter 100 proximate an end 102 of the adapter. Once the cap 200 is removed, fluid can pass through the adapter 200 to enable enteral feeding applications for example.

Figure 5:
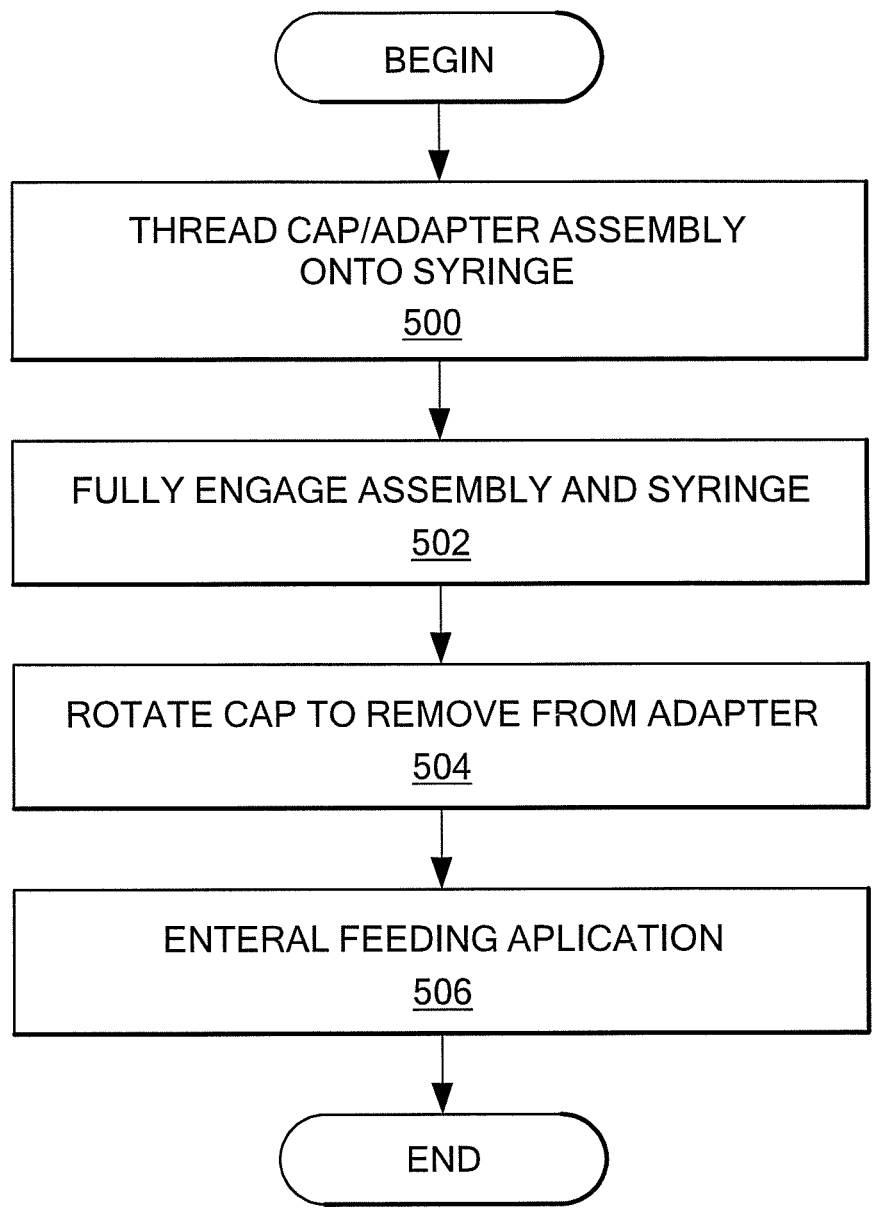
FIG. 5 is a flow diagram showing an exemplary sequence of steps for a syringe adapter in accordance with exemplary embodiments of the invention.

FIG. 5 shows an exemplary sequence of steps for providing a syringe adapter in accordance with exemplary embodiments of the invention. In step 500, a cap/adapter assembly is rotated in a first direction to thread the assembly onto a syringe. The cap includes an adapter engagement mechanism for coupling to a cap engagement mechanism of the adapter for enabling one-directional rotation of the cap/adapter assembly. In step 502, a mating mechanism of the adapter engages the threads of the syringe and the adapter is fully threaded onto the syringe. The mating mechanism resists rotation of the adapter in the opposite direction to prevent the adapter from being unthreaded from the syringe.

In step 504, the cap is rotated in the opposite direction so that the cap is pushed off the adapter. In an exemplary embodiment, this rotation breaks a seal between the cap and adapter to enable fluid to exit the syringe for allowing enteral feeding material to be ingested by a patient. In step 506, the adapted syringe is ready for enteral feeding applications.

Figure 3C:
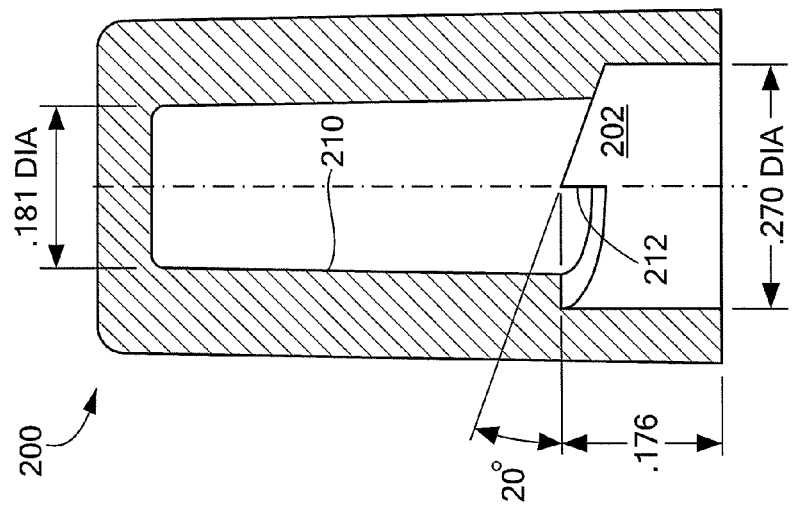
FIG. 3C is a partial cutaway view of a cap for a syringe adapter in accordance with exemplary embodiments of the invention.
Figure 3B:
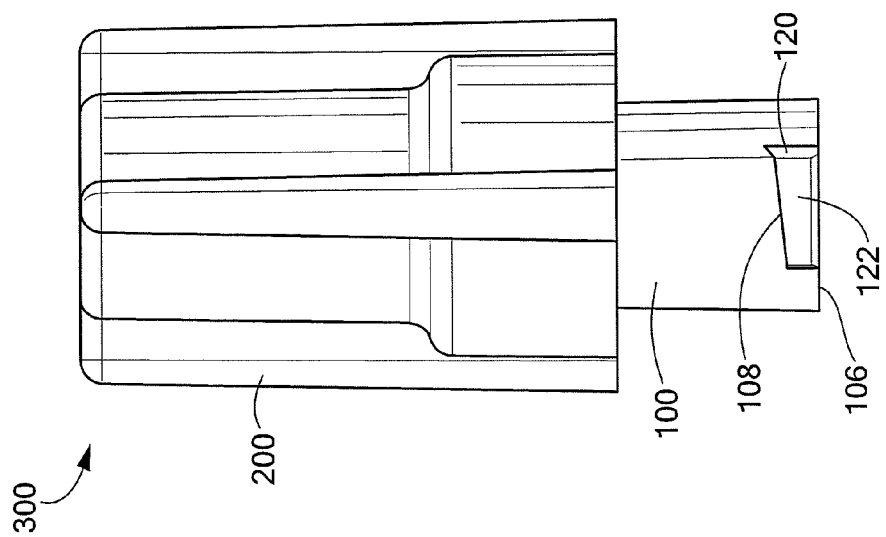
FIG. 3B is a side view of a syringe cap/adapter assembly in accordance with exemplary embodiments of the invention.
Figure 3D:
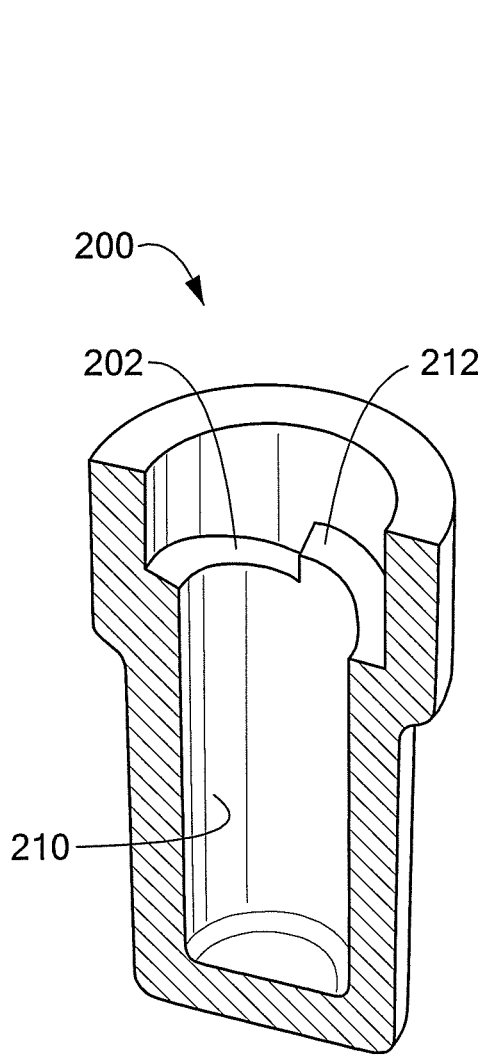
FIG. 3D is a perspective partial cutaway view of a cap for a syringe adapter in accordance with exemplary embodiments of the invention.

In general, the adapter and cap have dimensions sized to meet the needs of a particular application. In the exemplary embodiments contained here, the adapter and cap are shown and described for attachment to a standard IV syringe. FIG. 3C shows certain exemplary dimensions, in inches, for the cap 200, and by extension, the adapter 100. While the drawings may not be to scale, the drawings convey a general dimensional relationship between the components.

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A method comprising:
   providing an adapter having a first end and a second end and a cap engagement mechanism, the first end having a mating mechanism; and
   providing a cap having an adapter engagement mechanism to engage the cap engagement mechanism of the adapter;
   rotating the cap in a first direction to engage the adapter engagement mechanism and the cap engagement mechanism so that rotation of the cap in the first direction rotates the cap and the adapter;
   further rotating the cap in the first direction until the mating mechanism of the adapter is secured to a syringe such that the adapter cannot be removed without destruction of the syringe; and
   rotating the cap in a second direction opposite the first direction to remove the cap from the adapter.

2. The method according to claim 1, wherein the cap and adapter form a seal that is broken by rotation of the cap in the second direction.

3. The method according to claim 1, wherein the first end includes a tip configured for enteral feeding.

* * * * *